(12) United States Patent
Nolan et al.

US006365344B1

(10) Patent No.: US 6,365,344 B1
(45) Date of Patent: *Apr. 2, 2002

(54) METHODS FOR SCREENING FOR TRANSDOMINANT EFFECTOR PEPTIDES AND RNA MOLECULES

(75) Inventors: Garry P. Nolan, Menlo Park; S. Michael Rothenberg, Palo Alto, both of CA (US)

(73) Assignees: The Board of Trustees of the Leland Stanford Junior University, Palo Alto, CA (US); Rigel Pharmaceuticals, Inc., So. San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/589,109

(22) Filed: Jan. 23, 1996

(51) Int. Cl.⁷ .................. C12Q 1/68; C12Q 15/63; C12Q 15/11

(52) U.S. Cl. .................. 435/6; 435/69.1; 435/320.1; 536/23.4

(58) Field of Search ..................... 435/4, 6, 172.3, 435/320.1, 69.1

(56) References Cited

U.S. PATENT DOCUMENTS

| | | |
|---|---|---|
| 5,217,889 A | 6/1993 | Roninson et al. |
| 5,223,408 A | 6/1993 | Goeddel |
| 5,283,173 A | 2/1994 | Fields et al. |
| 5,639,595 A | 6/1997 | Mirabelli et al. .............. 435/6 |
| 5,723,287 A | 3/1998 | Russell |
| 6,153,380 A | 11/2000 | Nolan et al. |

FOREIGN PATENT DOCUMENTS

| | | |
|---|---|---|
| EP | 0334301 B1 | 9/1989 |
| EP | 0 383 620 | 8/1990 |
| WO | 86/05803 | 10/1986 |
| WO | 90/02809 | 3/1990 |
| WO | 91/17266 | 11/1991 |
| WO | 91/19818 | 12/1991 |
| WO | 92/05266 | 4/1992 |
| WO | 92/07071 | 4/1992 |
| WO | 93/08278 | 4/1993 |
| WO | 93/23569 | 11/1993 |
| WO | 94/06920 | 3/1994 |
| WO | 94/19478 | 9/1994 |
| WO | 95/04824 | 2/1995 |
| WO | 95/16054 | 6/1995 |
| WO | 96/23899 | 8/1996 |
| WO | 96/38553 | 12/1996 |
| WO | 96/40987 | 12/1996 |
| WO | 00/05406 | 2/2000 |

OTHER PUBLICATIONS

Rayner and Gonda, "A Simple and Efficient Procedure for Generating Stable Expression Libraries by cDNA Cloning in a Retroviral Vector," *Mol Cell Biol* 14(2):880–887 (Feb. 1994).

Gudkov et al., "Cloning mammalian genes by expression selection of genetic suppressor elements: Association of kinesin with drug resistance and cell immortalization," *Proc. Natl. Acad. Sci. USA* 91:3744–3748 (Apr. 1994).

Whiteway et al., "Dominant negative selection heterologous genes: Isolation of *Candida albicans* genes that interfere with *Saccharomyces cervisiae* mating factor–induced cell cycle arrest," *Proc. Natl. Acad. Sci. USA* 89:9410–9414 (Oct. 1992).

Roninson et al., "Genetic Suppressor Elements: New Tools for Molecular Oncology—Thirteenth Cornelius P. Rhoads Memorial Award Lecture," *Cancer Res* 55:4023–4028 (Sep. 1995).

Murphy and Efstratiadis, "Cloning vectors for expression of cDNA libraries in mammalian cells," *Proc. Natl. Acad. Sci. USA* 84:8277–8281 (Dec. 1987).

LaBean and Kauffman, "Design of synthetic gene libraries encoding random sequence proteins with desired ensemble characteristics," *Protein Science* 2:1249–1254 (1993).

Deng et al., "Basis for selection of improved carbohydrate–binding single–chain antibodies from synthetic gene libraries," *Proc. Natl. Acad. Sci. USA* 92:4992–4996 (May 1995).

Virnekäs et al., "Trinucleotide phosphoramidites: ideal reagents for the synthesis of mixed oligonucleotides for random mutagenesis," *Nucleic Acids Res* 22(25):5600–5607 (1994).

Ito et al., "A general method for introducing a series of mutations into cloned DNA using the polymerase chain reaction," *Gene* 102:67–70 (1991).

Stuhlmann et al., "Introduction of a selectable gene into different animal tissue by a retrovirus recombinant vector," *Proc. Natl. Acad. Sci. USA* 81:7151–7155 (Nov. 1984).

Winnacker, E–L, From genes to clones: *Introduction to Gene Technology*, Weinheim, New York: VCH, pp. 260–270 (1997).

Winnacker, E–L, From genes to clones: *Introduction to Gene Technology*, Weinheim, New York: VCH, p. 359 (1987).

(List continued on next page.)

*Primary Examiner*—John S. Brusca
(74) *Attorney, Agent, or Firm*—Flehr Hohbach Test Albritton & Herbert LLP; Robin M. Silva; Anne M. Shyjan

(57) ABSTRACT

Biochemical libraries are screened for transdominant intracellularly bioactive agents by expressing a molecular library of randomized nucleic acids as a plurality of corresponding expression products in a plurality of cells, each of the nucleic acids comprising a different nucleotide sequence, detecting a cell of the plurality of cells exhibiting a changed physiology in response to the presence in the cell of a transdominant expression product of the corresponding expressio products; and isolating the cell and/or transdominant expression product.

12 Claims, 4 Drawing Sheets

OTHER PUBLICATIONS

Winnacker, E–L, From genes to clones: *Introduction to Gene Technology*, Weinheim, New York: VCH, pp. 363–370 (1987).

Winnacker, E–L, From genes to clones: *Introduction to Gene Technology*, Weinheim, New York: VCH, pp. 373–374 (1987).

Caldecott, et al., "An Interaction Between the Mammalian DNA Repair Protein XRCC1 and DNA Ligase III," *Mol Cell Biol* 14(1):68–76 (1994).

Youssoufain, H, "Localization of Fanconi anemia C protein to the cytoplasm of mammalian cells," *Proc. Natl. Acad. Sci. USA* 91:7975–7979 (Aug. 1994).

Priority document, Denmark Patent Application No. 0629/95, titled "A Method for Identifcation of Biologically Active Peptides and Nucleic Acids" (Jun. 2, 1995).

Kim et al., "Diversified sequences of peptide epitope for same–RNA recognition," *Proc. Natl. Acad. Sci. USA* 90:10046–10050 (Nov. 1993).

Berkhout and Kalver, "In vivo selection of randomly mutated retroviral genomes," *Nucleic Acids Res.* 21(22):5020–5024 (1993).

Luzzago et al., "Mimicking of discontinuous epitopes by phage–displayed peptide. I. Epitope mapping of human H ferritin using a phage library of constrained peptides", *Gene* 128:51–57 (1993).

Wong et al., "High–Efficiency Identification of Genes by Functional Analysis from a Retroviral cDNA Expression Library", *J. Virology* 68(9):5523–5531 (1994).

Gudkov et al., "Isolation of genetic suppressor elements, inducing resistance to topoisomerase II–interactive cytotoxic drugs, from human topoisomeras II cDNA", *Proc. Natl. Acad. Sci. USA* 90(8):3231–3235 (1993).

Martin et al. The affinity–selection of a minibody polypeptide inhibitor of human interleukin–6. The Embo Journal vol. 13, pp. 5305–5309, 1994.*

Gavin et al. Major histocampatibility complex class I allele–specific peptide libraries: identification of peptides that mimic an H–Y T cell epitope. Eur. J. Immunol. vol. 24 pp. 2124–2133, 1994.*

Abbas et al. Chapter 11 "Cytokines" in Cellular and Molecular Immunology W.B. Saunders Co. Philadelphia, 1994.*

Cadwell and Joyce, "Randomization of Genes PCR Mutagenesis," Abstract excerpted from *PCR Methods and Applications*, 2(1):28–33 (1992) (Abstract No. XP 002033396).

Fong et al., "Scanning whole cells with phage–display libraries: Identification of peptide ligands that modulate cell function", Drug Dev. Res. 33: 64–70, 1994.*

Kitamura, T., et al., "Efficient Screening of Retroviral cDNA Expression Libraries," *PNAS, USA*, 92:9146–9150 (1995).

Pear et al. (Sep. 1993) Production of high–titer helper free retroviruses by transcient transfection, PNAS 90, p.8392–8396.

Hupp et al. (Oct. 20, 1995) Small Peptides Activate the Latent Sequence–Specific DNA Binding Function of p53, Cell 83, p.237–245.

Scott et al. (1994) Random Peptide Libraries, Current Opinion in Biotechnology 5, p40–48.

Palzkill et al. (Feb. 1994) Selection of Functional Signal Peptide Cleavage Sites from a Library of Random Sequences, J Bacteriology 176, p.563–568.

* cited by examiner

FIG._1

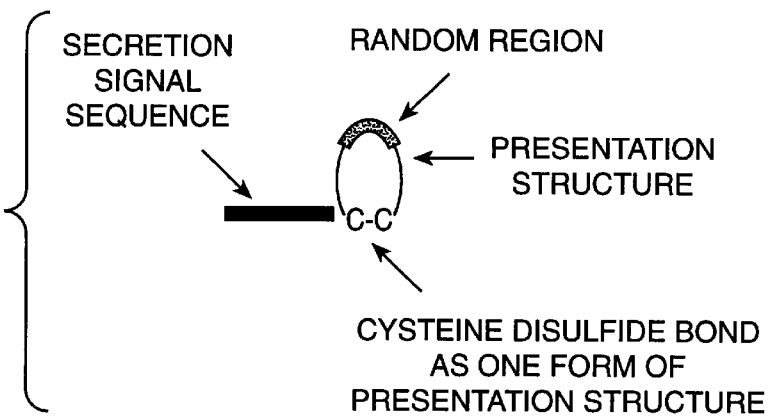
FIG._3A
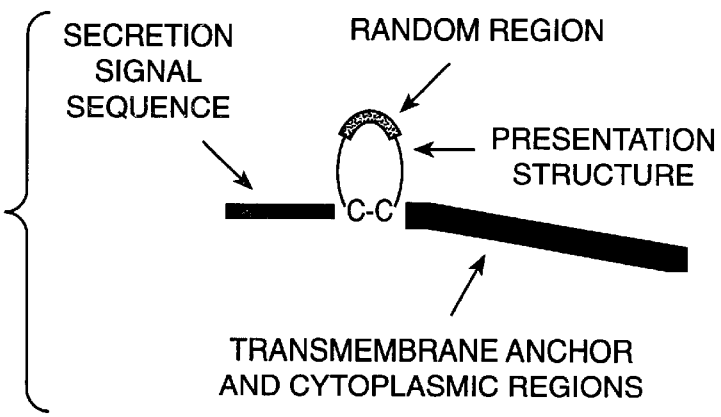
FIG._3B
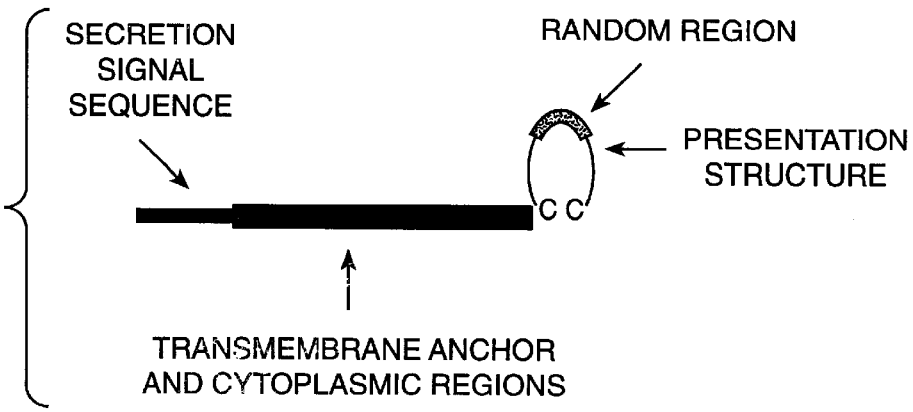
FIG._3C

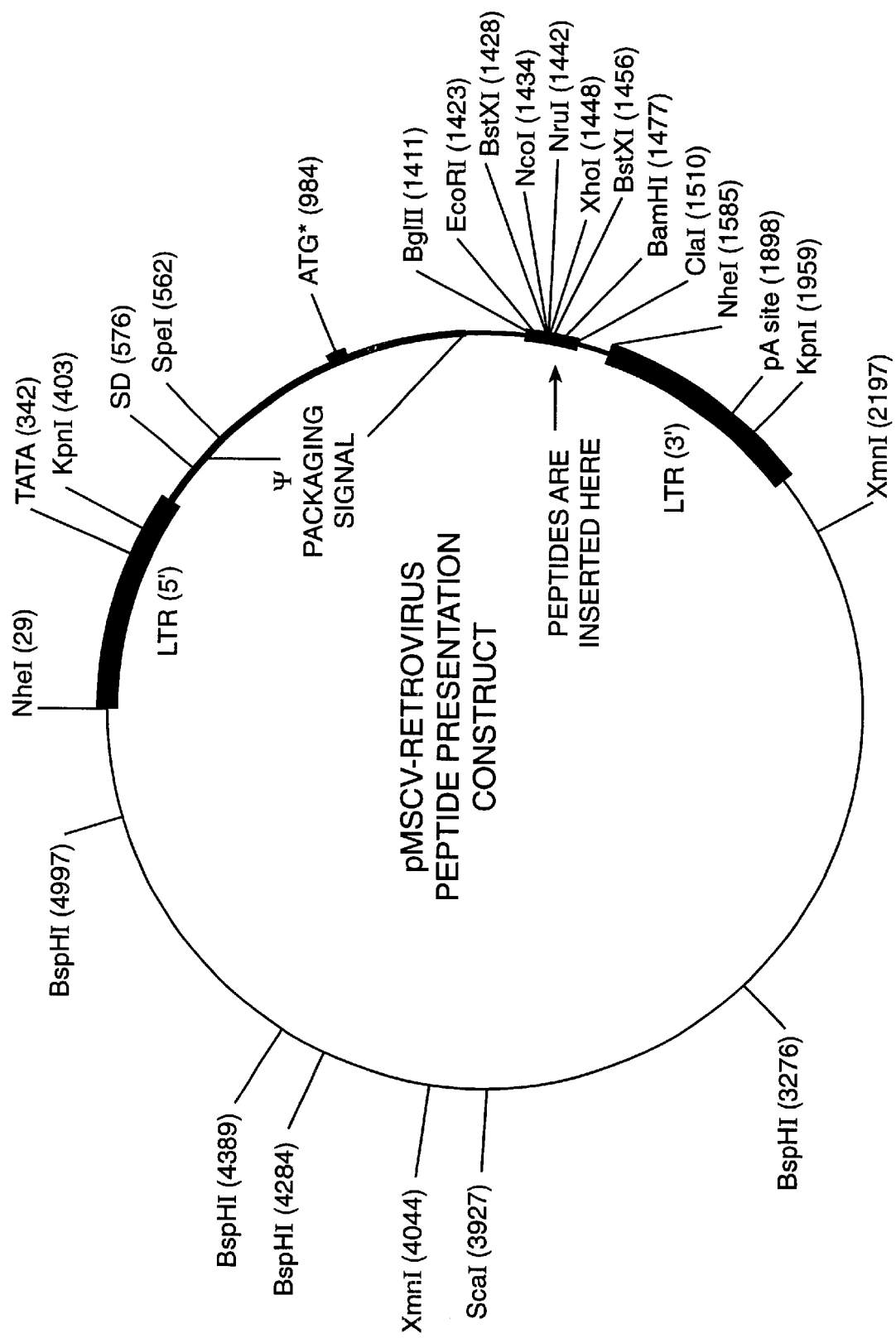
FIG._4

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
             (A) LENGTH: 9 amino acids
             (B) TYPE: amino acid
             (C) STRANDEDNESS:
             (D) TOPOLOGY: Not Relevant (ii) MOLECULE TYPE: peptide (xi) SEQUENCE DESCRIPTION: SEQ ID NO:1:

Xaa Xaa Xaa Pro Pro Xaa Pro Xaa Xaa
    1               5

(2) INFORMATION FOR SEQ ID NO:2:

(i) SEQUENCE CHARACTERISTICS:
             (A) LENGTH: 92 base pairs
             (B) TYPE: nucleic acid
             (C) STRANDEDNESS: double
             (D) TOPOLOGY: linear (ii) MOLECULE TYPE: cDNA (xi) SEQUENCE DESCRIPTION: SEQ ID NO:2:

GCTTAGCAAG ATCTCTACGG TGGACCKNNK NNKNNKNNKN NKNNKNNKNN KNNKNNCCCC        60

ACTCCCATGG TCCTACGTAC CACCACACTG GG                                     92

(2) INFORMATION FOR SEQ ID NO:3:

(i) SEQUENCE CHARACTERISTICS:
             (A) LENGTH: 34 base pairs
             (B) TYPE: nucleic acid
             (C) STRANDEDNESS: double
             (D) TOPOLOGY: linear (ii) MOLECULE TYPE: cDNA (xi) SEQUENCE DESCRIPTION: SEQ ID NO:3:

GCTTAGCAAG ATCTGTGTGT CAGTTAGGGT GTGG                                   34

(2) INFORMATION FOR SEQ ID NO:4:
```

(i) SEQUENCE CHARACTERISTICS:
    (A) LENGTH: 74 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:4:

```
CTGGAGAACC AGGACCATGG GCNNKNNKNN KNNKNNKNNK NNKNNKNNKN NKGGGCCCCC      60

TTAAACCATT AAAT                                                       74
```

(2) INFORMATION FOR SEQ ID NO:5:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
CTGGAGAACC AGGACCATGG GCNNKNNKNN KCCTCCCNNK CCTNNKNNKG GGCCCCCTTA      60

AACCATTAAA T                                                          71
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
TCATGCATCC AATTTAATGG TTTAAG                                          26
```

(2) INFORMATION FOR SEQ ID NO:7:

(i) SEQUENCE CHARACTERISTICS:
        (A) LENGTH: 4950 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
TGAAAGACCC CACCTGTAGG TTTGGCAAGC TAGCTTAAGT AACGCCATTT TGCAAGGCAT      60

GGAAAATACA TAACTGAGAA TAGAGAAGTT CAGATCAAGG TTAGGAACAG AGAGACAGCA     120

GAATATGGGC CAAACAGGAT ATCTGTGGTA AGCAGTTCCT GCCCCGGCTC AGGGCCAAGA     180

ACAGATGGTC CCCAGATGCG GTCCCGCCCT CAGCAGTTTC TAGAGAACCA TCAGATGTTT     240

CCAGGGTGCC CCAAGGACCT GAAAATGACC CTGTGCCTTA TTTGAACTAA CCAATCAGTT     300

CGCTTCTCGC TTCTGTTCGC GCGCTTCTGC TCCCCGAGCT CAATAAAAGA GCCCACAACC     360

CCTCACTCGG CGCGCCAGTC CTCCGATAGA CTGCGTCGCC CGGGTACCCG TATTCCCAAT     420

AAAGCCTCTT GCTGTTTGCA TCCGAATCGT GGACTCGCTG ATCCTTGGGA GGGTCTCCTC     480

AGATTGATTG ACTGCCCACC TCGGGGGTCT TTCATTTGGA GGTTCCACCG AGATTTGGAG     540

ACCCCTGCCT AGGGACCACC GACCCCCCCG CCGGGAGGTA AGCTGGCCAG CGGTCGTTTC     600
```

```
CTGTCTGTCT CTGTCTTTGT GCGTGTTTGT GCCGGCATCT AATGTTTGCG CCTGCGTCTG      660

TACTAGTTAG CTAACTAGCT CTGTATCTGG CGGACCCGTG GTGGAACTGA CGAGTTCTGA      720

ACACCCGGCC GCAACCCTGG GAGACGTCCC AGGGACTTTG GGGGCCGTTT TTGTGGCCCG      780

ACCTGAGGAA GGGAGTCGAT GTGGAATCCG ACCCCGTCAG GATATGTGGT TCTGGTAGGA      840

GACGAGAACC TAAAACAGTT CCCGCCTCCG TCTGAATTTT TGCTTTCGGT TTGGAACCGA      900

AGCCGCGCGT CTTGTCTGCT GCAGCGCTGC AGCATCGTTC TGTGTTCTCT CTGTCTGACT      960

GTGTTTCTGT ATTTGTCTGA AAATTAGGGC CAGACTGTTA CCACTCCCTT AAGTTTGACC     1020

TTAGGTCACT GGAAAGATGT CGAGCGGATC GCTCACAACC AGTCGGTAGA TGTCAAGAAG     1080

AGACGTTGGG TTACCTTCTG CTCTGCAGAA TGGCCAACCT TAACGTCGG ATGGCCGCGA      1140

GACGGCACCT TTAACCGAGA CCTCATCACC CAGGTTAAGA TCAAGGTCTT TTCACCTGGC     1200

CCGCATGGAC ACCCAGACCA GGTCCCCTAC ATCGTGACCT GGGAAGCCTT GGCTTTTGAC     1260

CCCCCTCCCT GGGTCAAGCC CTTTGTACAC CCTAAGCCTC CGCCTCCTCT TCCTCCATCC     1320

GCCCCGTCTC TCCCCCTTGA ACCTCCTCGT TCGACCCCGC CTCGATCCTC CCTTTATCCA     1380

GCCCTCACTC CTTCTCTAGG CGCCGGAATT CCAGGACCAT GGGCGGGCCC CCTTAAACCA     1440

TTAAATTGGT AAAATAAAGG ATCCGTCGAC CTGCAGCCAA GCTTATCGAT AAAATAAAAG     1500

ATTTTATTTA GTCTCCAGAA AAAGGGGGGA ATGAAAGACC CCACCTGTAG GTTTGGCAAG     1560

CTAGCTTAAG TAACGCCATT TTGCAAGGCA TGGAAAATAC ATAACTGAGA ATAGAGAAGT     1620

TCAGATCAAG GTTAGGAACA GAGAGACAGC AGAATATGGG CCAAACAGGA TATCTGTGGT     1680

AAGCAGTTCC TGCCCCGGCT CAGGGCCAAG AACAGATGGT CCCCAGATGC GGTCCCGCCC     1740

TCAGCAGTTT CTAGAGAACC ATCAGATGTT TCCAGGGTGC CCCAAGGACC TGAAAATGAC     1800

CCTGTGCCTT ATTTGAACTA ACCAATCAGT TCGCTTCTCG CTTCTGTTCG CGCGCTTCTG     1860

CTCCCCGAGC TCAATAAAAG AGCCCACAAC CCCTCACTCG GCGCGCCAGT CCTCCGATAG     1920

ACTGCGTCGC CCGGGTACCC GTGTATCCAA TAAACCCTCT TGCAGTTGCA TCCGACTTGT     1980

GGTCTCGCTG TTCCTTGGGA GGGTCTCCTC TGAGTGATTG ACTACCCGTC AGCGGGGGTC     2040

TTTCATTCGT AATCATGGTC ATAGCTGTTT CCTGTGTGAA ATTGTTATCC GCTCACAATT     2100

CCACACAACA TACGAGCCGG AAGCATAAAG TGTAAAGCCT GGGGTGCCTA ATGAGTGAGC     2160

TAACTCACAT TAATTGCGTT GCGCTCACTG CCCGCTTTCC AGTCGGGAAA CCTGTCGTGC     2220

CAGCTGCATT AATGAATCGG CCAACGCGCG GGGAGAGGCG GTTTGCGTAT TGGGCGCTCT     2280

TCCGCTTCCT CGCTCACTGA CTCGCTGCGC TCGGTCGTTC GGCTGCGGCG AGCGGTATCA     2340

GCTCACTCAA AGGCGGTAAT ACGGTTATCC ACAGAATCAG GGGATAACGC AGGAAAGAAC     2400

ATGTGAGCAA AAGGCCAGCA AAAGGCCAGG AACCGTAAAA AGGCCGCGTT GCTGGCGTTT     2460

TTCCATAGGC TCCGCCCCCC TGACGAGCAT CACAAAAATC GACGCTCAAG TCAGAGGTGG     2520

CGAAACCCGA CAGGACTATA AAGATACCAG GCGTTTCCCC CTGGAAGCTC CCTCGTGCGC     2580

TCTCCTGTTC CGACCCTGCC GCTTACCGGA TACCTGTCCG CCTTTCTCCC TTCGGGAAGC     2640

GTGGCGCTTT CTCATAGCTC ACGCTGTAGG TATCTCAGTT CGGTGTAGGT CGTTCGCTCC     2700

AAGCTGGGCT GTGTGCACGA ACCCCCCGTT CAGCCCGACC GCTGCGCCTT ATCCGGTAAC     2760

TATCGTCTTG AGTCCAACCC GGTAAGACAC GACTTATCGC CACTGGCAGC AGCCACTGGT     2820

AACAGGATTA GCAGAGCGAG GTATGTAGGC GGTGCTACAG AGTTCTTGAA GTGGTGGCCT     2880

AACTACGGCT ACACTAGAAG GACAGTATTT GGTATCTGCG CTCTGCTGAA GCCAGTTACC     2940
```

-continued

```
TTCGGAAAAA GAGTTGGTAG CTCTTGATCC GGCAAACAAA CCACCGCTGG TAGCGGTGGT    3000

TTTTTTGTTT GCAAGCAGCA GATTACGCGC AGAAAAAAAG GATCTCAAGA AGATCCTTTG    3060

ATCTTTTCTA CGGGGTCTGA CGCTCAGTGG AACGAAAACT CACGTTAAGG GATTTTGGTC    3120

ATGAGATTAT CAAAAAGGAT CTTCACCTAG ATCCTTTTAA ATTAAAAATG AAGTTTTAAA    3180

TCAATCTAAA GTATATATGA GTAAACTTGG TCTGACAGTT ACCAATGCTT AATCAGTGAG    3240

GCACCTATCT CAGCGATCTG TCTATTTCGT TCATCCATAG TTGCCTGACT CCCCGTCGTG    3300

TAGATAACTA CGATACGGGA GGGCTTACCA TCTGGCCCCA GTGCTGCAAT GATACCGCGA    3360

GACCCACGCT CACCGGCTCC AGATTTATCA GCAATAAACC AGCCAGCCGG AAGGGCCGAG    3420

CGCAGAAGTG GTCCTGCAAC TTTATCCGCC TCCATCCAGT CTATTAATTG TTGCCGGGAA    3480

GCTAGAGTAA GTAGTTCGCC AGTTAATAGT TTGCGCAACG TTGTTGCCAT TGCTACAGGC    3540

ATCGTGGTGT CACGCTCGTC GTTTGGTATG GCTTCATTCA GCTCCGGTTC CCAACGATCA    3600

AGGCGAGTTA CATGATCCCC CATGTTGTGC AAAAAAGCGG TTAGCTCCTT CGGTCCTCCG    3660

ATCGTTGTCA GAAGTAAGTT GGCCGCAGTG TTATCACTCA TGGTTATGGC AGCACTGCAT    3720

AATTCTCTTA CTGTCATGCC ATCCGTAAGA TGCTTTTCTG TGACTGGTGA GTACTCAACC    3780

AAGTCATTCT GAGAATAGTG TATGCGGCGA CCGAGTTGCT CTTGCCCGGC GTCAATACGG    3840

GATAATACCG CGCCACATAG CAGAACTTTA AAAGTGCTCA TCATTGGAAA ACGTTCTTCG    3900

GGGCGAAAAC TCTCAAGGAT CTTACCGCTG TTGAGATCCA GTTCGATGTA ACCCACTCGT    3960

GCACCCAACT GATCTTCAGC ATCTTTTACT TTCACCAGCG TTTCTGGGTG AGCAAAAACA    4020

GGAAGGCAAA ATGCCGCAAA AAAGGGAATA AGGGCGACAC GGAAATGTTG AATACTCATA    4080

CTCTTCCTTT TTCAATATTA TTGAAGCATT TATCAGGGTT ATTGTCTCAT GAGCGGATAC    4140

ATATTTGAAT GTATTTAGAA AAATAAACAA ATAGGGGTTC CGCGCACATT TCCCCGAAAA    4200

GTGCCACCTG ACGTCTAAGA AACCATTATT ATCATGACAT TAACCTATAA AAATAGGCGT    4260

ATCACGAGGC CCTTTCGTCT CGCGCGTTTC GGTGATGACG GTGAAAACCT CTGACACATG    4320

CAGCTCCCGG AGACGGTCAC AGCTTGTCTG TAAGCGGATG CCGGGAGCAG ACAAGCCCGT    4380

CAGGGCGCGT CAGCGGGTGT TGGCGGGTGT CGGGGCTGGC TTAACTATGC GGCATCAGAG    4440

CAGATTGTAC TGAGAGTGCA CCATATGCGG TGTGAAATAC CGCACAGATG CGTAAGGAGA    4500

AAATACCGCA TCAGGCGCCA TTCGCCATTC AGGCTGCGCA ACTGTTGGGA AGGGCGATCG    4560

GTGCGGGCCT CTTCGCTATT ACGCCAGCTG GCGAAAGGGG GATGTGCTGC AAGGCGATTA    4620

AGTTGGGTAA CGCCAGGGTT TTCCCAGTCA CGACGTTGTA AAACGACGGC CAGTGCCACG    4680

CTCTCCCTTA TGCGACTCCT GCATTAGGAA GCAGCCCAGT AGTAGGTTGA GGCCGTTGAG    4740

CACCGCCGCC GCAAGGAATG GTGCATGCAA GGAGATGGCG CCCAACAGTC CCCCGGCCAC    4800

GGGGCCTGCC ACCATACCCA CGCCGAAACA AGCGCTCATG AGCCCGAAGT GGCGAGCCCG    4860

ATCTTCCCCA TCGGTGATGT CGGCGATATA GGCGCCAGCA ACCGCACCTG TGGCGCCGGT    4920

GATGCCGGCC ACGATGCGTC CGGCGTAGAG                                    4950
```

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:8:

Pro Lys Lys Lys Arg Lys Val
1               5

(2) INFORMATION FOR SEQ ID NO:9:

(i) SEQUENCE CHARACTERISTICS:
           (A) LENGTH: 20 amino acids
           (B) TYPE: amino acid
           (C) STRANDEDNESS:
           (D) TOPOLOGY: Not Relevant (ii) MOLECULE TYPE: peptide (xi) SEQUENCE DESCRIPTION: SEQ ID NO:9:

Ala Val Lys Arg Pro Ala Ala Thr Lys Lys Ala Gly Gln Ala Lys Lys
1               5                   10                  15

Lys Lys Leu Asp
            20

(2) INFORMATION FOR SEQ ID NO:10:

(i) SEQUENCE CHARACTERISTICS:
           (A) LENGTH: 4 amino acids
           (B) TYPE: amino acid
           (C) STRANDEDNESS:
           (D) TOPOLOGY: Not Relevant (ii) MOLECULE TYPE: peptide (xi) SEQUENCE DESCRIPTION: SEQ ID NO:10:

Gly Gly Pro Pro
1

(2) INFORMATION FOR SEQ ID NO:11:

(i) SEQUENCE CHARACTERISTICS:
           (A) LENGTH: 48 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:11:

ATGGGAAAGA AGAAGAAGAA GAAGAAGAAG AAGAAGGGGG GGCCCCCC                48

(2) INFORMATION FOR SEQ ID NO:12:

(i) SEQUENCE CHARACTERISTICS:
           (A) LENGTH: 30 base pairs
           (B) TYPE: nucleic acid
           (C) STRANDEDNESS: unknown
           (D) TOPOLOGY: unknown (ii) MOLECULE TYPE: cDNA (xi) SEQUENCE DESCRIPTION: SEQ ID NO:12:

CCTCCTCCTC CTCCTCCTCC TCCTCCTCCT                                   30

(2) INFORMATION FOR SEQ ID NO:13:

(i) SEQUENCE CHARACTERISTICS:
           (A) LENGTH: 30 base pairs
           (B) TYPE: nucleic acid
           (C) STRANDEDNESS: unknown
           (D) TOPOLOGY: unknown -continued

```
    (ii) MOLECULE TYPE: cDNA (ix) FEATURE:
         (A) NAME/KEY: misc_feature
         (B) LOCATION: 3..4
         (D) OTHER INFORMATION: /note= "The 'N' appearing at
             position 3, as well as at positions 6, 9, 12, 15, 18, 21,
             24, 27 and 30, can be either A,C,T or G."

(xi) SEQUENCE DESCRIPTION: SEQ ID NO:13:

GGNGGNGGNG GNGGNGGNGG NGGNGGNGGN                                              30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 3..4
         (D) OTHER INFORMATION: /note= "The 'N' appearing at
             position 3, as well as at positions 6, 9, 12, 15, 18, 21,
             24, 27 and 30, can be either A, C, T or G."

(xi) SEQUENCE DESCRIPTION: SEQ ID NO:14:

TTNTTNTTNT TNTTNTTNTT NTTNTTNTTN                                              30
```

METHODS FOR SCREENING FOR TRANSDOMINANT EFFECTOR PEPTIDES AND RNA MOLECULES

TECHNICAL FIELD

The technical field of this invention is methods for screening for transdominant effector peptides and RNA molecules selected inside living cells from randomized pools.

BACKGROUND

Signaling pathways in cells often begin with an effector stimulus that leads to a phenotypically describable change in cellular physiology. Despite the key role intracellular signaling pathways play in pathogenesis, in most cases, little is understood about a signaling pathway other than the initial stimulus and the ultimate cellular response.

Historically, signal transduction has been analyzed by biochemistry or genetics. The biochemical approach dissects a pathway in a "stepping-stone" fashion: find a molecule that acts at, or is involved in, one end of the pathway, isolate assayable quantities and then try to determine the next molecule in the pathway, either upstream or downstream of the isolated one. The genetic approach is classically a "shot in the dark": induce or derive mutants in a signaling pathway and map the locus by genetic crosses or complement the mutation with a cDNA library. Limitations of biochemical approaches include a reliance on a significant amount of pre-existing knowledge about the constituents under study and the need to carry such studies out in vitro, post-mortem. Limitations of purely genetic approaches include the need to first derive and then characterize before proceeding with identifying and cloning the gene.

Screening molecular libraries of chemical compounds for drugs that regulate signaling systems has led to important discoveries of great clinical significance. Cyclosporin A (CsA) and FK506, for examples, were selected in standard pharmaceutical screens for inhibition of T-cell activation. It is noteworthy that while these two drugs bind completely different cellular proteins—cyclophilin and FK506 binding protein (FKBP), respectively, the effect of either drug is virtually the same—profound and specific suppression of T-cell activation, phenotypically observable in T cells as inhibition of mRNA production dependent on transcription factors such as NF-AT and NF-κB. Libraries of small peptides have also been successfully screened in assays for bioactivity. The literature is replete with examples of small peptides capable of modulating a wide variety of signaling pathways. For example, a peptide derived from the HIV-1 envelope protein has been shown to block the action of cellular calmodulin.

A major limitation of conventional in vitro screens is delivery. While only minute amounts of an agent may be necessary to modulate a particular cellular response, delivering such an amount to the requisite subcellular location necessitates exposing the target cell or system to relatively massive concentrations of the agent. The effect of such concentrations may well mask or preclude the targeted response.

The present invention provides methods and compositions to create, effectively introduce into cells and screen compounds that affect a signaling pathway. Little or no knowledge of the pathway is required, other than a presumed signaling event and an observable physiologic change in the target cell. The disclosed methods are conceptually distinct from prior library search methods in that it is an in vivo stratagem for accessing intracellular signaling mechanisms. The invention also provides for the isolation of the constituents of the pathway, the tools to characterize the pathway, and lead compounds for pharmaceutical development.

Relevant Literature

Mann et al. (1983) Cell 33, 153–159, Pear et al. (1993) Proc. Natl. Acad. Sci. USA 90(18):8392–6 and copending U.S. patent application Ser. No. 08/023,909 describe the BOSC and BING retroviral systems useful as delivery vectors for the disclosed methods.

Scott and Craig (1994) Current Opinion in Biotechnology 5:40–48 review random peptide libraries. Hupp et al. (1995) describe small peptides which activate the latent sequence-specific DNA binding function of p53. Palzkill et al. (1994) report the selection of functional signal cleavage sites from a library of random sequences introduced into TEM-1-lactamase.

SUMMARY OF THE INVENTION

The invention provides methods and compositions for screening for transdominant intracellularly bioactive agents such as pharmaceuticals. The invention accesses molecules or targets within living cells and provides for the direct selection of those bioactive agents with desired phenotypic effects. The general methods involve steps: expressing a molecular library of randomized nucleic acids as a plurality of isolated corresponding randomized expression products in a plurality of cells, each of the nucleic acids comprising a different nucleotide sequence, screening for a cell of the plurality of cells exhibiting a changed physiology in response to the presence in the cell of a transdominant expression product of the corresponding expression products; and detecting and isolating the cell and/or transdominant expression product, In a particular embodiment, the expressing step comprises translating the nucleic acids and/or corresponding transcripts, and each of the nucleic acids encodes a peptide comprising a different amino acid sequence. The nucleic acids may be joined to sequences encoding polypeptide backbones of artificial design capable of intracellularly presenting randomized peptides as structured domains. The methods may also involve introducing the library into the cells, such as through the use of retroviral vectors, and particularly suitable vectors are also disclosed.

BRIEF DESCRIPTION OF THE FIGURES

FIG. 3. Presentation constructs for localizing presentation structures to specific cellular locales.

FIG. 4. Schematic of a retroviral construct.

DETAILED DESCRIPTION OF THE INVENTION

Figure 1:
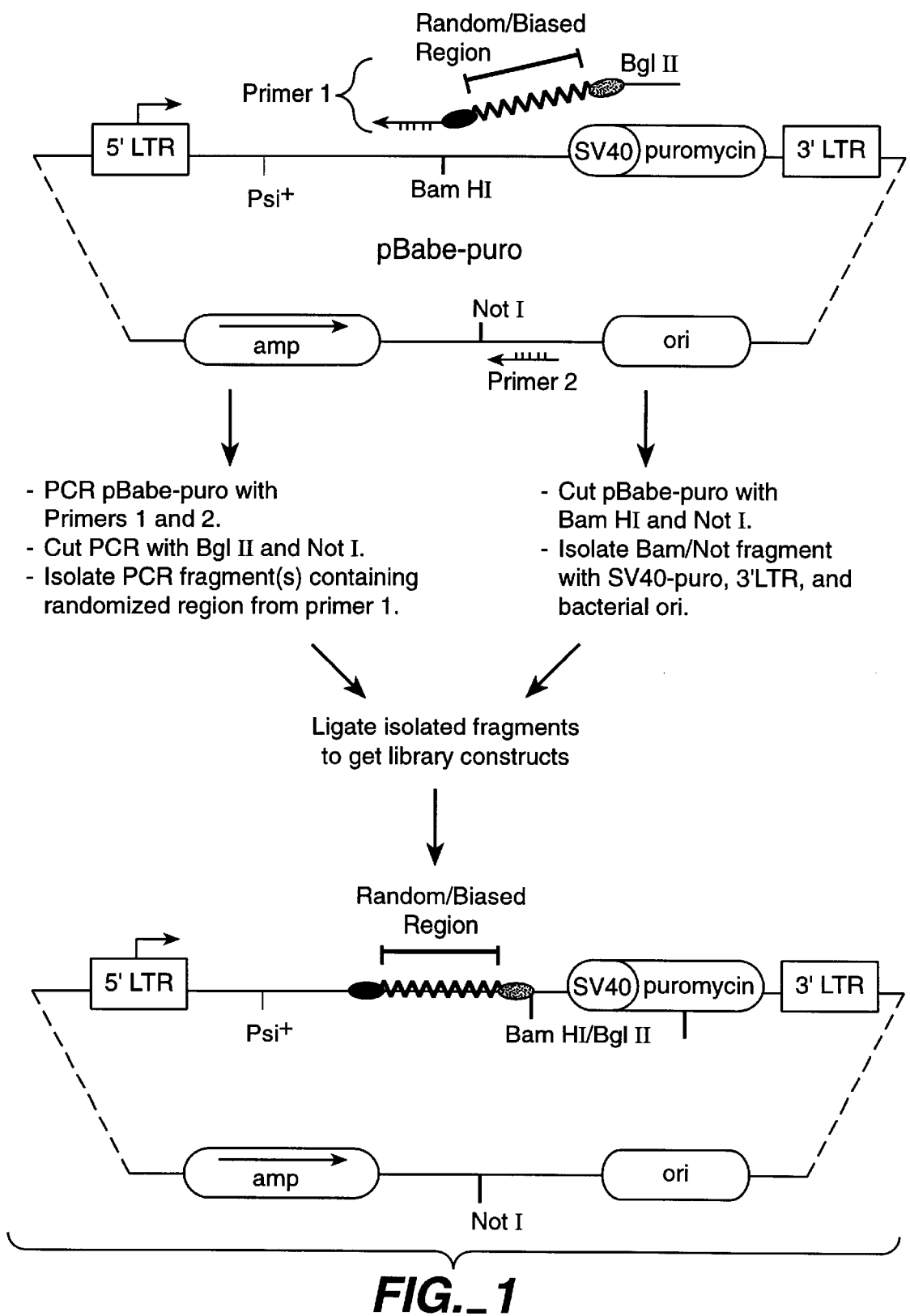
FIG. 1. Creation of a library of random peptides in a retrovirus DNA construct by PCR.

The subject methods generally involve introducing a molecular library of randomized nucleic acids into a population of cells. The introduced nucleic acids are randomized and expressed in the cells as a library of isolated randomized expression products, which may be nucleic acids, such as message, antisense RNA, ribozyme components, etc., or peptides. The library should provide a sufficiently structurally diverse population of randomized expression products to effect a probabilistically sufficient range of cellular responses to provide one or more cells exhibiting a desired response. Generally at least $10^6$, preferably at least $10^7$ more preferably at least $10^8$ and most preferably at least $10^9$ different expression products are simultaneously analyzed in the subject methods. Preferred methods maximize library size and diversity.

The introduced nucleic acids and resultant expression products are randomized, meaning that each nucleic acid and peptide consists of essentially random nucleotides and amino acids, respectively. The library may be fully random or biased, e.g. in nucleotide/residue frequency generally or per position. For example, a biased library may encode peptides for interactions with known classes of molecules, such as SH-3 domain proteins, as defined by peptides containing XXXPPXPXX (where X=randomized residues, SEQ ID No. 1). In other embodiments, the nucleotides or residues are randomized within a defined class, e.g. of hydrophobic amino acids, of purines, etc. In any event, where the ultimate expression product is a nucleic acid, at least 10, preferably at least 12, more preferably at least 15, most preferably at least 21 nucleotide positions need to be randomized; more if the randomization is less than perfect. Similarly, at least 5, preferably at least 6, more preferably at least 7 amino acid positions need to be randomized; again, more if the randomization is less than perfect.

An important aspect of the invention is the functional and structural isolation of the randomized expression products. This is important to facilitate subsequent drug development and optimization. Generally, isolation is effected by providing free (not covalently coupled) expression product, though in some situations, the expression product may be coupled to a functional group or fusion partner, preferably a heterologous (to the host cell) or synthetic (not native to any cell) functional group or fusion partner. Exemplary groups or partners include signal sequences capable of constitutively localizing the expression product to a predetermined subcellular locale such as the Golgi, endoplasmic reticulum, nucleoli, nucleus, nuclear membrane, mitochondria, chloroplast, secretory vesicles, lysosome, etc.; binding sequences capable of binding the expression product to a predetermined protein while retaining bioactivity of the expression product; sequences signaling selective degradation, of itself or co-bound proteins; secretory and membrane-anchoring signals; etc.

It may also be desirable to provide a partner which conformationally restricts the randomized expression product to more specifically define the number of structural conformations available to the cell. For example, such a partner may be a synthetic presentation structure: an artificial polypeptide capable of intracellularly presenting a randomized peptide as a conformation-restricted domain. Generally such presentation structures comprise a first portion joined to the N-terminal end of the randomized peptide, and a second portion joined to the C-terminal end of the peptide. Preferred presentation structures maximize accessibility to the peptide by presenting it on an exterior loop, for example of coiled-coils, (Myszka, D. G., and Chaiken, I. M. Design and characterization of an intramolecular antiparallel coiled coil peptide. Biochemistry. 1994. 33:2362–2372). To increase the functional isolation of the randomized expression product, the presentation structures are selected or designed to have minimal biologically active as expressed in the target cell. In addition, the presentation structures may be modified, randomized, and/or matured to alter the presentation orientation of the randomized expression product. For example, determinants at the base of the loop may be modified to slightly modify the internal loop peptide tertiary structure, while maintaining the absolute amino acid identity. Other presentation structures include zinc-finger domains, loops on beta-sheet turns and coiled-coil stem structures in which non-critical residues are randomized; loop structures held together by cysteine bridges, cyclic peptides, etc.

Following expression of the library in the targeted cells, cells exhibiting a changed physiology in response to the presence in such cells of a transdominant expression product are detected and isolated. A transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κnB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-1, or Herpes viridae family members, or Respiratory SyncytiaVirus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In general, cis-effects are effects within molecules wherein elements that are interacting are covalently joined to each other although these elements might individually manifest themselves as separable domains. Trans-effects (transdominant in that under some cellular conditions the desired effect is manifested) are those effects between distinct molecular entities, such that molecular entity A, not covalently linked to molecular entity B, binds to or otherwise has an effect upon the activities of entity B. As such, most known pharmacological agents are transdominant effectors.

A wide variety of phenotypic changes may be targeted, such as changes in the amount or distribution of cellular differentiation markers, e.g. T/B-cell activation, cell growth or death, membrane potentials, etc. Similarly, a wide variety of techniques may be used to isolate cells exhibiting changed physiology in response to the presence of a library expression product, such as FACS, lysis selection using complement, cell cloning, etc. Where the randomized expression product is expressed on the extracellular surface of the host cell or is secreted by the host cell into the extracellular medium, the methods may involve screening for a change in the physiology of a "responder cell" in the vicinity of the host cell, exhibiting a changed physiology in response to the presence of the surface-expressed or secreted expression product. Alternatively, the methods may involve screening for a "target cell" in the vicinity of the host cell, that specifically binds the surface-expressed or secreted expression product.

A wide variety of cells may be used depending on the nature of the targeted cellular pathway, so long as the cell is suitably transfectable with the library and may be monitored for the targeted physiological changes. The method of introduction is largely dictated by the targeted cell type. Exemplary methods include $CaPO_4$ precipitation, liposome fusion, lipofectin®, electroporation, viral infection, etc. As many pharmaceutically important screens require human or model mammalian cell targets, retroviral vectors capable of transfecting such targets are frequently employed. A particularly well-suited retroviral transfection system is described in Mann et al. (1983) Cell 33, 153–159, Pear et al. (1993) Proc. Natl. Acad. Sci. USA 90(18):8392–6 and copending U.S. patent application Ser. No. 08/023,909, now abandoned.

In one embodiment of the invention, the library is generated in a retrovirus DNA construct backbone. Preferred techniques for constructing such libraries are described in more detail below. Libraries with up to $10^9$ unique sequences can be readily generated in such DNA backbones. After generation of the library in DNA, and its isolation from bacteria, it is converted into infectious virus. Conversion into infectious virus requires the delivery of the library DNA to a retrovirus packaging system. Such systems can include BOSC23, PhiNX-eco, PhiNX-ampho, 293T+gag-pol and retrovirus envelope, PA317, and other extant packaging systems. Methods for high-efficiency packaging of retroviral libraries (cDNA) are described in Kitamura et al. (1995) *Efficient screening of retroviral cDNA libraries*. PNAS 92:9146–9150. Libraries containing up to $10^7$ retrovirus particles per ml were derived in this system. Scaling up these methods conveniently yields $10^9$ individual and unique library components in a 100 ml reaction. The library of retroviruses is then used to infect the target cells by any of a number of different protocols, e.g. see Kitamura et al supra for details on some infection protocols Depending upon how the particular resident expression product(s) effect the target molecule function, the physiology of the cell will be affected in differing ways. Since extremely large libraries of different molecular peptide or RNA shapes can be delivered to cells via retroviral transduction, this embodiment of the invention provides a high frequency for the isolation of cells affected in a predetermined manner. For instance, peptides that inhibit T cell activation processes are readily isolated using a population of Jurkat cells, e.g. Jurkat-NFAT-dipA, engineered to express diphtheria toxin under the control of Nuclear Factor of Activated T cells (NFAT) regulatory elements. Unproductively transduced cells are killed when NFAT is activated through the T cell receptor and other signaling mechanisms specific to T cells (Serafini AT et al. (1995). *Isolation of mutant T lymphocytes with defects in capacitative calcium entry*. Immunity, 3(2):239–50). This is because NFAT activation leads to transcription and translation of diphtheria toxin A chain in these cells, which efficiently kills them. However, productive mutations in the NFAT activation pathway are rescued. This approach has already been used to isolate mutants in T cell signaling pathways. Peptide or compound expression libraries are also used to mimic mutation of the signaling pathway leading to activation of NFAT, i.e. peptides which interfere with signaling of the NFAT pathway by binding to and inhibiting the function of a required signaling protein or factor can block programmed cell death.

The following experimental section/examples are offered by way of illustration and not by way of limitation.

EXPERIMENTAL

Retroviral Presentation Construct for Peptide Expression

A series of retroviral constructs have been designed for expression of randomized and biased peptides within target cell populations. The peptide is expressed from a retroviral promoter. The translation unit has several important components. Glycine following the initiator methionine at the amino terminus stabilizes the peptide and enhances cytoplasmic half-life, according to Varshavsky's N-End Rule. In some constructs, a nine amino acid flu epitope tag has been incorporated to permit co-precipitation of the rare peptide and any molecule to which it has affinity, by using monoclonal antibodies to the epitope. Glycines are encoded before and after the random/biased expression product encoding regions to provide some molecular flexibility. Two carboxyl-terminal prolines are encoded to confer stability to carboxypeptidase.

For construction of a large library two primers were made (schematized in FIG. 1). The first, designated the random peptide primer, consists of 1) a complementary region for vector priming, 2) the regions mentioned above, and 3) a random or biased expression product region, here presented as a 30 base sequence encoding a peptide of length 10 amino acids. In addition, we have inserted a stop codon in all three reading frames in case of minor deletions or insertions in the random region. The design of the primer ensures a glycine/proline termination in most reading frames. The second primer is downstream in the vector and primes a region of the plasmid that contains a unique Not I site. These primers are used to create a library of fragments, each containing a different nucleotide sequence that each potentially encodes a different peptide. These families of fragments are ligated to vector fragments containing puromycin selection sequence, a 3' LTR , and a bacterial origin of replication. The ligation products are then electroporated into E. coli and DNA is prepared from the resulting library. Using this technique we have constructed independent random libraries with up to $2 \times 10^8$ unique inserts. Sequencing of multiple individual inserts demonstrates they have the structure as defined by Primer 1, and the peptides encoded are random. Such libraries thus made contain subsets of the total $10^{13}$ predicted peptides.

Generation of Retroviral Peptide Libraries

Figure 2:
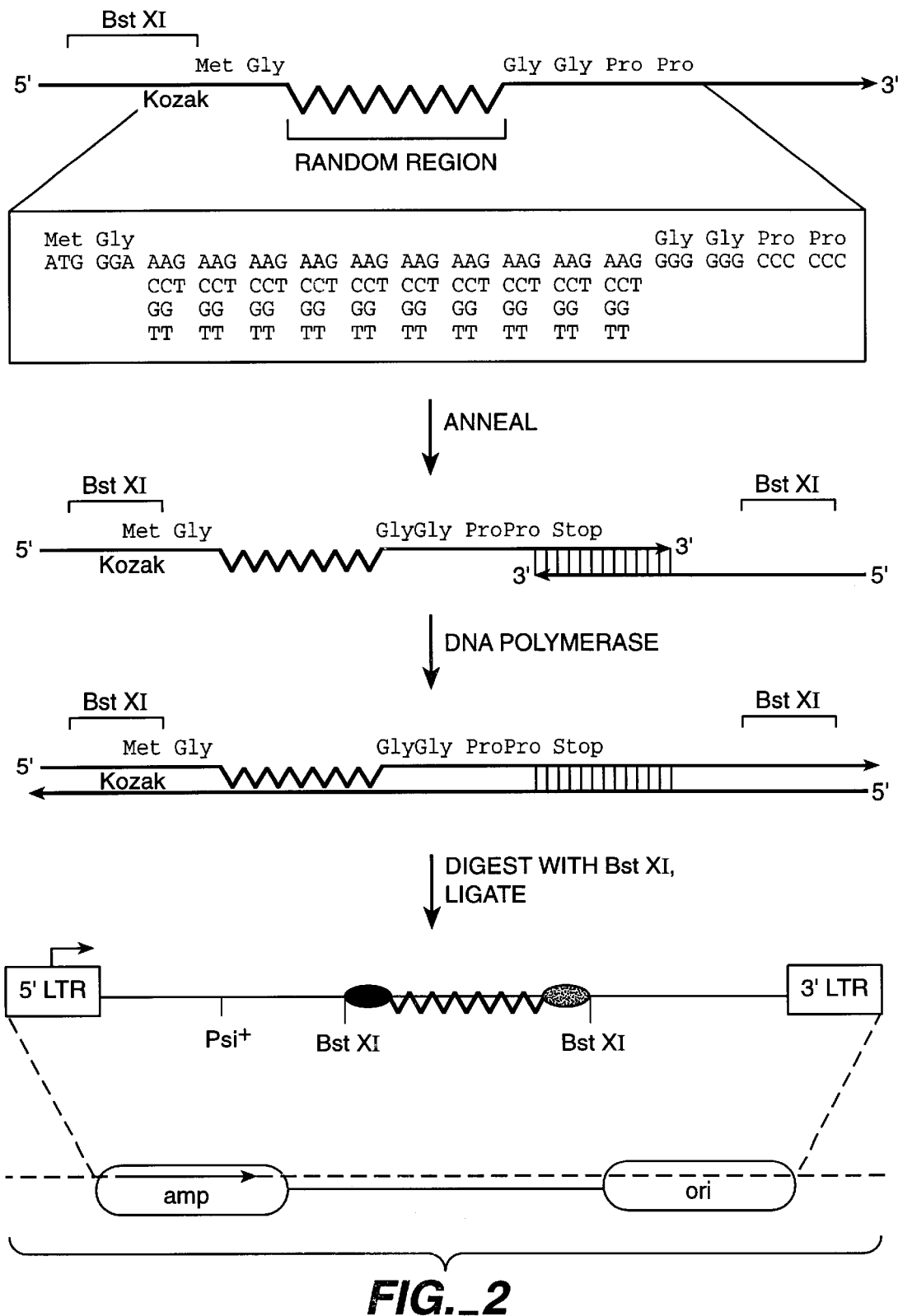
FIG. 2. Creation of a library of random peptides in a retrovirus DNA construct by primed DNA synthesis (SEQ ID NOS.10–14).

A scheme for generating a peptide library in the pBabe Puro vector is shown in FIG. 2. Primers for PCR were synthesized, purified and deprotected according to standard protocols. Primer 1, complementary to polylinker sequences in the pBabe Puro retroviral construct, has the sequence 5' GCT TAG CAA GAT CTC TAC GGT GGA CCK NNK NNK NNK NNK NNK NNK NNK NNK NNK NNC CCC ACT CCC ATG GTC CTA CGT ACC ACC ACA CTG GG 3' (SEQ ID NO.2). N represents any of the four bases; K is limited to G or T. Primer 2 has the sequence 5' GCT TAG CAA GAT CTG TGT GTC AGT TAG GGT GTGG 3' (SEQ ID NO.3) and is complementary to sequences within the pUC 18 origin of replication. PCR was carried out for 8 rounds using primer 1, primer 2, pBabe Puro as template, and a mixture of Taq DNA Polymerase (Promega) and Deep Vent DNA Polymerase (New England Biolabs) in a ratio of 128 Taq: 1 Deep Vent as described in Barnes (1994) Proc. Natl. Acad. Sci. USA, 91, pp. 2216–2220. The amplified PCR product was purified, digested with restriction enzymes Bgl II and Not I (Promega), purified again and ligated with the corresponding Bam HI-Not I fragment of pBabe Puro. After transformation the resulting library contained ~2×10$^8$ clones, greater than 80% of which contained inserts.

pMSCV-PC and pBabeMN-PC retroviral construct libraries:

Oligonucleotides were synthesized and purified according to standard protocols. The "library" oligonucleotides have the sequence 5' CTG GAG AAC CAG GAC CAT GGG C (NNK)$_{10}$ GGG CCC CCT TAA ACC ATT AAA T 3' (SEQ ID NO.4) or 5' CTG GAG AAC CAG GAC CAT GGG CNN KNN KNN KCC TCC CNN KCC TNN KNN KGG GCC CCC TTA AAC CAT TAA AT 3' (SEQ ID NO.5). A third oligonucleotide ("constant"), complementary to the 3' ends of the library oligonucleotides, has the sequence 5' TCA TGC ATC CAA TTT AAT GGT TTA AG 3' (SEQ ID NO.6). As shown in FIG. 2, each library oligonucleotide is annealed to the constant oligonucleotide, converted to double stranded DNA with Sequenase (United States Biochemical) or Klenow (Promega), digested with restriction enzyme Bst XI (New England Biolabs), and purified and ligated with the appropriate Bst XI-digested retroviral construct. Transformation efficiencies are ~2×10$^8$ clones per microgram of ligated DNA, greater than 90% of which contain an insert. A representative retrovirus is shown in FIG. 4; see also, retroviral vector with presentation construct nucleotide sequence (SEQ ID NO.7).

Peptide Library Infection of a Factor-dependent Line and Outgrowth of an Apoptosis-Resistant Line The Baf/3 cell line is an IL-3 dependent cell that undergoes rapid apoptosis in the absence of IL-3. Thus it makes an attractive cell line for dominant effector peptides. Cells expressing a peptide that inhibits apoptosis are readily selected against the background of dying cells. We chose this cell line as a model for demonstrating peptide selection.

A retroviral library containing 5×10$^6$ independent peptide inserts was transfected into BOSC23 cells and converted into retrovirus with an approximate titer of 5×10$^5$ per ml. Twelve ml of viral supernatant was used to infect 6×10$^6$ Baf/3cells (2 ml per infection of 1×10$^6$ cells in 6 independent infections). Cells were grown for 3 days after infection in the presence of IL-3 to allow retroviral integration and peptide expression. After three days IL-3 was withdrawn and the cells allowed to grow for two weeks. After two weeks, one well of six had outgrowth of cells that survive in the absence of IL-3, indicating the presence of an apoptosis-inhibiting peptide. Peptides derived in this manner may effect the IL-3 independence by positive dominancy (i.e. mimic or circumvent the positive regulatory role of IL-3) or by inhibition (i.e. prevent the apoptosis process upon IL-3 withdrawal).

Subcellular Targeting

In some embodiments of the invention, expression products are localized to, or preferentially concentrated in, different subcellular compartments within cells, e.g. by using appropriate addition of addressins to a peptide presentation construct, see, FIG. 3. Addressins are available for a wide variety of subcellular locales including the nucleus, Golgi, mitochondria, plasma membranes, endoplasmic reticulum, secretory granules, secreted, cell surface (extracellular domain with random), cell surface (intracellular domain random), etc. For example, many proteins whose functions require entry into the cell nucleus include nuclear localization signal (NLS) sequences: generally short, positively charged (basic) domains that serve to direct the entire protein in which they occur to the cell's nucleus. Numerous NLS amino acid sequences have been reported including single basic NLS's such as that of the SV40 (monkey virus) large T antigen (Pro Lys Lys Lys Arg Lys Val (SEQ ID NO.8)), Kalderon (1984), et al., Cell, 39:499–509, and double basic NLS 's exemplified by that of the Xenopus (African clawed toad) protein, nucleoplasmin (Ala Val Lys Arg Pro Ala Ala Thr Lys Lys Ala Gly Gln Ala Lys Lys LysLys Leu Asp (SEQ ID NO.9)), Dingwall, et al., Cell, 30:449–458, 1982 and Dingwall, et al., J.Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, etal., Proc, Natl. Acad, Sci, USA, 84:6795–6799, 1987; Galileo, et al., Proc. Natl. Acad. Sci. USA, 87:458–462, 1990.

Secreted Peptide Structure

In some embodiments of the invention, it is desired to generate a peptide capable of binding to the surface of, or affecting the physiology of, a target cell that is other than the host cell, e.g the cell infected with the retrovirus. In this case the peptide library is configured with a secretion signal sequence at its amino terminus, usually clipped off after secretion, such that the peptide is ultimately secreted into the extracellular space. Secretory signal sequences and their transferability to unrelated proteins are well known, e.g. Silhavy et al.(1985) Microbiol Rev 49, 398–418. In a preferred approach, a fusion product is configured to contain, in series, secretion signal peptide-presentation structure-randomized expression product region-presentation structure, see FIG. 3. In this manner, target cells grown in the vicinity of cells caused to express the library of peptides, are bathed in secreted peptide. Target cells exhibiting a physiological change in response to the presence of a peptide, e.g. by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Surface-expressed Peptide Structure

In certain embodiments of the invention, it is desirable to localize the randomized peptides to the surface of a cell. The invention provides methods for presenting the randomized expression product extracellularly or in the cytoplasmic space; see FIG. 3. For extracellular presentation, a modification of the secreted structure above is made; specifically, a membrane anchoring region is provided at the carboxyl terminus of the peptide presentation structure. The anchor can be a transmembrane domain, such as that found in a variety of surface expressed molecules of the Ig family (e.g. CD4, CD8, IgM, T cell receptor), or a lipid anchoring region such as found in Thy-1. Other anchoring domains exist and are known to those who practice in the art. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening a molecular library of nucleic acids comprising randomized sequences for a nucleic acid encoding an extracellular transdominant bioactive peptide, said method comprising the steps of:

introducing said library in retroviral vectors into a first plurality of mammalian cells;

expressing said library as a plurality of corresponding extracellular candidate transdominant bioactive peptides in said first plurality of mammalian cells, wherein the candidate peptides are expressed with a secretion signal sequence which is not native to said first plurality of mammalian cells;

contacting a second plurality of mammalian cells with said candidate peptides;

screening said second plurality of mammalian cells for a cell exhibiting a changed physiology in response to a transdominant bioactive peptide expressed by said first plurality of mammalian cells; and detecting said cell exhibiting a changed physiology; whereby, said molecular library is screened.

2. A method of screening a molecular library of nucleic acids comprising randomized sequences for a nucleic acid encoding a transdominant bioactive peptide, said method comprising the steps of:

expressing said library as a plurality of corresponding candidate transdominant bioactive peptides in a first plurality of mammalian cells, wherein the candidate peptides are expressed with a secretion signal sequence which is not native to said first plurality of mammalian cells;

screening said first plurality of mammalian cells or a second plurality of mammalian cells which are co-cultured with said first plurality of mammalian cells or are contacted with said candidate peptides, for a cell exhibiting a changed physiology in response to the presence of a transdominant bioactive peptide expressed by said first plurality of mammalian cells; and detecting said cell exhibiting a changed physiology; whereby, said molecular library is screened.

3. A method of screening a molecular library of nucleic acids comprising randomized sequences for a nucleic acid encoding a transdominant bioactive peptide, said method comprising the steps of:

expressing said library as a plurality of corresponding candidate transdominant bioactive peptides in a first plurality of mammalian cells, wherein the candidate peptides are expressed with a fusion partner which is not native to said first plurality of mammalian cells and wherein the candidate peptides are secreted from said first plurality of mammalian cells;

screening said first plurality of mammalian cells or a second plurality of mammalian cells which are co-cultured with said first plurality of mammalian cells or are contacted with said candidate peptides with said fusion partner, for a cell exhibiting a changed physiology in response to the presence of a transdominant bioactive peptide expressed by said first plurality of mammalian cells; and detecting said cell exhibiting a changed physiology; whereby, said molecular library is screened.

4. A method of screening a molecular library of nucleic acids comprising randomized sequences for a nucleic acid encoding a transdominant bioactive peptide, said method comprising the steps of:

expressing said library as a plurality of corresponding candidate transdominant bioactive peptides in a first plurality of mammalian cells, wherein the candidate peptides are expressed with a fusion partner which is not native to said first plurality of mammalian cells and wherein the candidate peptides are secreted from said first plurality of mammalian cells;

screening said first plurality of mammalian cells or a second plurality of mammalian cells which are co-cultured with said first plurality of mammalian cells or are contacted with said candidate peptides with said fusion partner, for a cell exhibiting a changed physiology in response to the presence of a transdominant bioactive peptide expressed by said first plurality of mammalian cells;

detecting said cell exhibiting a changed physiology; and isolating a target molecule that binds to said transdominant bioactive peptide;

whereby, said molecular library is screened.

5. The method according to claim 3 or claim 4 wherein said fusion partner is a secretory signal sequence which effects the secretion of the candidate peptides.

6. A method of screening a molecular library of nucleic acids comprising randomized sequences for a nucleic acid encoding an extracellular transdominant bioactive peptide, said method comprising the steps of:

introducing said library in retroviral vectors into a first plurality of mammalian cells;

expressing said library as a plurality of corresponding extracellular candidate transdominant bioactive peptides in said first plurality of mammalian cells, wherein the candidate peptides are expressed with a secretion signal sequence which is not native to said first plurality of mammalian cells;

contacting a second plurality of mammalian cells with said candidate peptides;

screening said second plurality of mammalian cells for a cell exhibiting a changed physiology in response to a transdominant bioactive peptide expressed by said first plurality of mammalian cells;

detecting a cell exhibiting a changed physiology; and isolating a target molecule that binds to said transdominant bioactive peptide;

whereby, said molecular library is screened.

7. A method of screening a molecular library of nucleic acids comprising randomized sequences for a nucleic acid encoding a transdominant bioactive peptide, said method comprising the steps of:

expressing said library as a plurality of corresponding candidate transdominant bioactive peptides in a first plurality of mammalian cells, wherein the candidate peptides are expressed with a secretion signal sequence which is not native to said first plurality of mammalian cells;

screening said first plurality of mammalian cells or a second plurality of mammalian cells which are co-cultured with said first plurality of mammalian cells or are contacted with said candidate peptides, for a cell exhibiting a changed physiology in response to the presence of a transdominant bioactive peptide expressed by said first plurality of mammalian cells;

detecting said cell exhibiting a changed physiology; and isolating a target molecule that binds to said transdominant bioactive peptide;

whereby, said molecular library is screened.

8. The method according to claim 1, 2, 3, 4, 6 or 7 further comprising isolating said cell exhibiting a changed physiology.

9. The method according to claim 1, 2, 3, 4, 6 or 7 further comprising isolating said transdominant bioactive peptide.

10. The method according to claim 1, 2, 3, 4, 6 or 7 wherein said library comprises at least $10^6$ different nucleic acids.

11. The method according to claim 1, 2, 3, 4, 6 or 7 wherein said library comprises at least $10^7$ different nucleic acids.

12. The method according to claim 1, 2, 3, 4, 6 or 7 wherein said library comprises at least $10^8$ different nucleic acids.

* * * * *

UNITED STATES PATENT AND TRADEMARK OFFICE
CERTIFICATE OF CORRECTION

PATENT NO.      : 6,365,344 B1
DATED           : April 2, 2002
INVENTOR(S)     : Garry P. Nolan and Michael Rothenberg It is certified that error appears in the above-identified patent and that said Letters Patent is hereby corrected as shown below:

<u>Title page,</u>
Item [57], ABSTRACT,
Line 9, "expressio" should read -- expression --
Item [56], References Cited, OTHER PUBLICATIONS,
"Winnacker, E-L, From genes to clones: *Introduction to Gene Technology*, Weinheim, New York: VCH, pp. 260-270 (1997)" should read
-- Winnacker, E-L, From genes to clones: *Introduction to Gene Technology*, Weinheim, New York: VCH, pp. 260-270 (1987) --
"Youssoufain, H" should read -- Youssoufian, H --
"Gudkov et al." "human topoisomeras" should read -- human topoisomerase --
Please add
-- Kaufman, "Vectors Used for Expression in Mammalian Cells," *Meth. Enzymol.* 185:487-511 (1990) --
Please add
-- Nilsson et al., "Fusion proteins in biotechnology and structural biology," *Curr. Opin. Struc. Biol.* 2:569-575 (1992) --
Please add
-- Jellis et al., "Defining critical residues in the epitope for a HIV-neutralizing monoclonal antibody using phage display and peptide array technologies," *Gene* 137:63-68 (1993) --
Please add
-- Drucker et al., "Generation of a large library of point mutations in polyoma middle T antigen," *Nuc. Acids Res.* 19(24):6855-6861 (1991) --
Please add
-- van den Hazel et al., "Random Substitution of Large Parts of the Propeptide of Yeast Proteinase A," *J. Biol. Chem.* 270(15):8602-8609 (1995) --
Please add
-- Caldwell et al., "Molecular determinants of bioactivity of the Saccharomyces cerevisiae lipopeptide mating pheromone," *J. Biol. Chem.* 31:19817-23 (1994) --
Please add
-- Groger et al., "Directional antisense and sense cDNA cloning using Epstein-Barr virus episomal expression vectors," *Gene* 81(2):285-94 (1989) --
Please add
-- Yang, "Protein-peptide interactions analyzed with the yeast two-hybrid system," *Nuc. Acids Res.* 23(7):1152-6 (1995) --

UNITED STATES PATENT AND TRADEMARK OFFICE
CERTIFICATE OF CORRECTION

PATENT NO.    : 6,365,344 B1
DATED         : April 2, 2002
INVENTOR(S)   : Garry P. Nolan and Michael Rothenberg It is certified that error appears in the above-identified patent and that said Letters Patent is hereby corrected as shown below:

OTHER PUBLICATIONS, (cont'd)
Please add
-- Cull et al., "Screening for receptor ligands using large libraries of peptides linked to the C terminus of the *lac* repressor," *Proc. Nat. Acad. Sci.* 89:1865-69 (1992) --

Column 8,
Line 31, "etal.," should read -- et al., --

Signed and Sealed this

First Day of April, 2003

JAMES E. ROGAN
*Director of the United States Patent and Trademark Office*